United States Patent [19]

Light et al.

[11] 4,193,895

[45] Mar. 18, 1980

[54] AROMATIZATION PROCESS AND CATALYST

[75] Inventors: Steven D. Light, Fullerton; John W. Ward, Yorba Linda, both of Calif.

[73] Assignee: Union Oil Company of California, Los Angeles, Calif.

[21] Appl. No.: 932,468

[22] Filed: Aug. 10, 1978

Related U.S. Application Data

[63] Continuation-in-part of Ser. No. 842,221, Oct. 14, 1977, abandoned.

[51] Int. Cl.$^2$ .............................................. B01J 27/10
[52] U.S. Cl. .................................. 252/441; 252/442; 208/139; 585/419
[58] Field of Search ..................... 208/139; 260/673.5; 252/441, 442

[56] References Cited

U.S. PATENT DOCUMENTS

| | | | |
|---|---|---|---|
| 2,848,377 | 8/1958 | Webb | 252/441 X |
| 2,972,644 | 2/1961 | Holmes et al. | 252/474 X |
| 2,987,560 | 6/1961 | Holmes et al. | 252/446 PT X |
| 3,761,428 | 9/1973 | Sugier et al. | 252/466 PT |
| 3,790,473 | 2/1974 | Rausch | 252/441 X |
| 3,915,846 | 10/1975 | Wilhelm | 252/441 X |
| 3,992,465 | 11/1976 | Juguin et al. | 208/65 X |
| 4,133,839 | 1/1979 | Hayes | 260/666 A |
| 4,139,570 | 2/1979 | Antos | 260/666 A |

*Primary Examiner*—Patrick Garvin
*Attorney, Agent, or Firm*—Lannas S. Henderson; Gregory F. Wirzbicki; Dean Sandford

[57] ABSTRACT

Paraffinic, olefinic and naphthenic hydrocarbons are converted to aromatic hydrocarbons by contacting the same at elevated temperatures with a catalyst comprising an alumina-supported composite of platinum, chlorine and a minor proportion of cesium, with or without other added metals such as iridium, rhodium, rhenium and the like.

10 Claims, 1 Drawing Figure

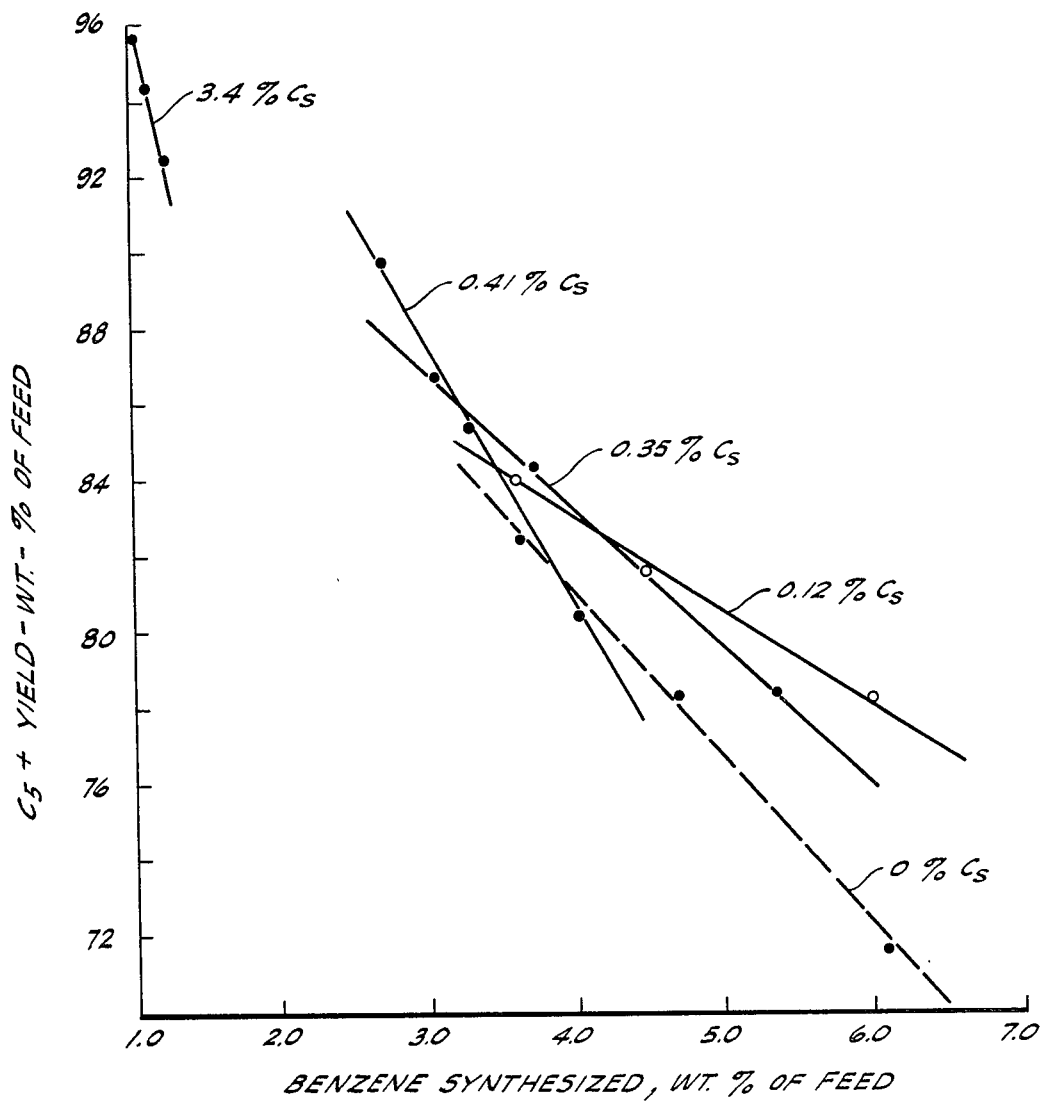

AROMATIZATION PROCESS AND CATALYST

RELATED APPLICATIONS

This application is a continuation-in-part of Ser. No. 842,221, filed Oct. 14, 1977 and now abandoned.

BACKGROUND AND SUMMARY OF INVENTION

In the catalytic reforming of naphthas to produce high-octane gasoline, and in the dehydrocyclization of $C_6$–$C_{12}$ paraffinic and olefinic hydrocarbons to produce benzene and alkyl benzenes, catalysts comprising platinum supported on a chlorided alumina base have long been used. The chloride component contributes an acid function which promotes hydrocracking, paraffin isomerization and dehydrocyclization reactions. For high severity operations in which maximum dehydrocyclization of paraffins is desired, the concomitant hydrocracking reactions can severely reduce liquid yields and lead to excessive dry gas ($C_1$–$C_3$) production. The isomerization of paraffins to more highly branched isoparaffins can also reduce yields of desired aromatic hydrocarbons, since paraffins which do not contain at least 6 carbon atoms with a straight chain of at least 5 carbon atoms will not readily cyclize, but tend instead to hydrocrack. For these and other reasons it would be desirable to moderate the acid function of the chloride component so as to reduce its hydrocracking and isomerization activity while retaining substantial dehydrocyclization activity. Even in cases where dehydrocyclization is not the main objective but in which some selective hydrocracking of heavy ends is desired, as for example in the reforming of high end-point naphthenic naphthas, it is often desirable to moderate the hydrocracking activity of the catalyst in order to reduce dry gas make.

In dehydrocyclization processes as such, it has been suggested at one extreme that instead of chloriding platinum-alumina catalysts, they should actually be essentially completely poisoned for cracking activity by the addition thereto of an alkali metal. While this practice does reduce cracking, it also drastically reduces dehydrocyclization activity, to the point that at the present time chlorided catalysts are found under proper conditions to give superior product distributions. The successful moderation of cracking activity, while retaining good dehydrocyclization activity of chlorided Pt—$Al_2O$ catalysts is the primary objective of the present invention - an objective which we have found is not achieved by merely reducing the chloride content of the catalyst.

We have now discovered that prior art catalysts comprising chlorided platinum-alumina composites are substantially improved in dehydrocyclization selectivity as opposed to non-selective cracking by incorporating therein certain small amounts of cesium, less than the atomic proportion of chloride in the catalyst. The reason for this improvement is uncertain, but it can be hypothesized that cesium, being the most strongly alkaline of the metals, may selectively poison the strongest acid sites on the catalyst which promote non-selective cracking to dry gas. Its large atomic radius may also be an operative steric factor. Other alkali metals such as sodium are found to give some smaller degree of improved selectivity, but only at high temperatures entailing low liquid yields. Cesium however is effective over a wide range of temperatures and conversion levels.

In some naphtha reforming operations, it is economically desirable to maximize the yield of $C_6$–$C_8$ aromatic hydrocarbons for the petrochemicals market. Maximizing aromatics production, particularly benzene, requires severe reforming conditions in order to achieve substantial dehydrocyclization of $C_6$–$C_{12}$ paraffins, which conditions also tend to reduce $C_5^+$ yields as a result of cracking. The catalysts of this invention are particularly designed to achieve the objectives of high $C_6$–$C_8$ aromatic yields and high $C_5^+$ yields in this type of reforming. They are also very active and selective for dehydrocyclization of the $C_6$–$C_{12}$ paraffins and olefins having a straight chain of at least 5 carbon atoms, to produce products such as benzene, toluene, xylenes, ethylbenzene, etc. For these and other operations the catalyst also preferably contains a very small proportion of one or more stabilizing metals such as iridium, rhodium, rhenium, etc.

PRIOR ART

U.S. Pat. No. 3,790,473 discloses dehydrocyclization and reforming processes utilizing a Pt—Ir—Re—Sn—$Al_2O_3$ catalyst, which may contain added Cl or an alkali metal. There is no disclosure of catalysts containing both Cl and an alkali metal.

U.S. Pat. Nos. 2,848,377 and 3,761,428 disclose the use of Pt—Ir—$Al_2O_3$—Cl catalysts for the reforming of naphthas to high octane gasoline, but do not disclose the use of any alkali metal, or of reforming for maximum aromatic production.

U.S. Pat. No. 3,992,465 discloses the use of Pt—Ir—$Al_2O_3$—Cl catalysts for the dehydrocyclization of paraffinic hydrocarbons, but does not disclose any alkali metal catalyst component.

U.S. Pat. No. 2,987,560 discloses the dehydrocyclization of paraffinic hydrocarbons using as the catalyst an alkali metal-poisoned Pt—$Al_2O_3$ catalyst. Sufficient alkali metal is used to completely neutralize any chloride acidity which may be present.

DETAILED DESCRIPTION

The catalysts employed herein fall within the following composition ranges:

| Component, Wt. % | Broad Range | Preferred Range |
|---|---|---|
| Pt | 0.1–2 | 0.3–1.0 |
| Cl | 0.1–3.0 | 0.5–2.0 |
| Cs | (1) | (2) |
| Support | Balance | |

(1)Sufficient to provide a Cs/Cl atomic ratio of about 0.005–0.2. (range, 0.0019–2.25 wt. %)
(2)Sufficient to provide a Cs/Cl atomic ratio of about 0.010–0.15. (range, 0.0038–1.69 wt. %)

The support material is preferably alumina xerogel, but may comprise mixtures of alumina with minor proportions of silica, zirconia, titania or the like. Conventional catalyst preparation techniques are employed, usually involving at least two separate impregnations of calcined 1/32–⅛ inch diameter alumina extrudates with aqueous solutions of the metal salts and additional chloride if required. The cesium is separately impregnated, preferably in the form of a solution of cesium nitrate, cesium chloride, cesium carbonate, etc. A preferred procedure consists in first impregnating the support with an aqueous solution of $H_2PtCl_6$ and HCl if required to give the desired Cl content in the finished catalyst, drying at about 100°–250° F., and then impregnating with an aqueous solution of CsNO₃, followed by final drying and calcination at about 800°–1200° F. However, suitable catalysts have been prepared by first impregnating with cesium, drying and then either simultaneously or sequentially impregnating with Pt and any other desired components.

Preferred catalysts of this invention also comprise small proportions, about 0.02–0.5 wt. %, preferably about 0.05–0.25 wt. %, of iridium and/or rhodium. These metals contribute thermal stability to the catalyst, which is particularly desirable in the case of high severity operations carried out at average bed temperatures above about 925° F. They may be incorporated into the catalyst by conventional methods, as e.g. impregnation with aqueous solutions of $H_2IrCl_6$ and/or $H_2RhCl_6$, either sequentially or simultaneously with impregnation of the Pt component. In addition to, or in lieu of iridium and rhodium, similar proportions of other metals known to enhance stability and/or selectivity of Pt—$Al_2O_3$ reforming catalysts may be incorporated, e.g. rhenium, manganese, gallium, indium, germanium, tin, zinc, nickel, cobalt, iron, etc.

The finished catalysts are particularly useful for the severe reforming of naphthas boiling between about 125°–420° F., preferably about 150°–375° F. Preferably the naphtha feed should comprise a substantial proportion, i.e. at least about 30 weight-percent of $C_6$–$C_{12}$ paraffin hydrocarbons, such as are normally found in straight-run naphthas. Suitable reforming-dehydrocyclization conditions for such feeds fall within the following ranges:

| Reforming - Dehydrocyclization Conditions | Broad Range | Preferred Range |
|---|---|---|
| Temp., °F. (Av. Bed) | 850–1150 | 900–1050 |
| H₂ Pressure, psi | 25–500 | 50–250 |
| LHSV, v/v/hr | 0.5–5 | 1–3 |
| H₂/oil, SCF/B | 100–6000 | 1000–4000 |

The selection of optimum conditions from the above ranges will of course depend upon a great variety of factors related to feed and catalyst composition, market economy and the like. Those skilled in the art will readily understand that severe process combinations will increase the yield of $C_6$–$C_8$ aromatics while decreasing $C_5$+ yields, and vice versa.

Under the foregoing conditions, adequate catalyst activity is usually maintained for periods of 3–10 days, whereupon the catalyst is oxidatively regenerated and rejuvenated by oxychlorination as described for example in U.S. Pat. Nos. 3,981,823 and 4,044,955. Presently available data indicates that at least about 50 of such reforming-regeneration-oxychlorination cycles are feasible before replacement of the catalyst becomes necessary as a result of unfavorable product distribution ratios.

For the dehydrocyclization of pure or mixed $C_7$–$C_{12}$ paraffins the same general process conditions and preferences described above are utilized. However, for the dehydrocyclization of n-hexane, temperatures in the range of about 950°–1100° F. are preferred.

The following examples are illustrative of the invention:

EXAMPLES 1–5

A base catalyst was first prepared by impregnating 1/16 inch diameter extrudates of gamma alumina with an aqueous solution containing dissolved therein sufficient $H_2PtCl_6$, $H_2IrCl_6$, and HCl to give final Pt, Ir and Cl contents of 0.6%, 0.10% and 1.2% by weight, respectively. The extrudates were drained, dried at about 250° F., and divided into several lots which were then separately impregnated with aqueous solutions of cesium nitrate of varying concentration, calculated to give four final catalysts of the following compositions:

Table 1

| Catalyst | A | B | C | D |
|---|---|---|---|---|
| Pt, wt. % | 0.6 | 0.6 | 0.6 | 0.6 |
| Ir, wt. % | 0.1 | 0.1 | 0.1 | 0.1 |
| Cl, wt. % | 1.2 | 1.2 | 1.2 | 1.2 |
| Cs, wt. % | 0.12 | 0.35 | 0.41 | 3.4 |
| Cs/Cl Atomic Ratio | 0.0265 | 0.077 | 0.091 | 0.75 |

After calcination for 1 hour at 1050° F., each of the foregoing catalysts, as well as a sample of the base catalyst containing no Cs, were activity tested for the reforming-dehydrocyclization of a blend of a straight run naphtha and a catalytically cracked naphtha, the blend having the following characteristics:

| Feed Characteristics | |
|---|---|
| Gravity, °API | 59.0 |
| Boiling Range, °F. | 155–362 |
| Octane No. (Res. Calculated) | 64.5 |
| Sulfur | 0.88 ppm |
| Nitrogen | 0.7 ppm |

| Hydrocarbon Components, Wt. % | | |
|---|---|---|
| Paraffinic, total | | 55.8 |
| n-Hexane | 7.14 | |
| $C_7$ | 15.31 | |
| $C_8$ | 10.54 | |
| $C_9$ | 7.10 | |
| $C_{10}$ | 3.67 | |
| Naphthenic, total | | 20.11 |
| Cyclohexane | 1.03 | |
| Cyclo $C_7$ | 6.51 | |
| Cyclo $C_8$ | 4.19 | |
| Cyclo $C_9$ | 2.66 | |
| Cyclo $C_{10}$ | 2.01 | |
| Aromatic, total | | 24.01 |
| Benzene | 1.43 | |
| Toluene | 5.15 | |
| $C_8$ | 9.48 | |
| $C_9$ | 5.78 | |
| $C_{10}$ | 1.65 | |

Each catalyst was tested at 925°, 950°, and 975° F., and in all runs at 2.0 LHSV, 225 psig, and 5000 SCF H₂/barrel. The $C_1$–$C_3$ and $C_5$ yields, and yields of benzene synthesized (over and above benzene present in the feed) were as follows:

Table 2

| | Temp., °F. | | |
|---|---|---|---|
| Yields, Wt.% of Feed | 925 | 950 | 975 |
| Base Catalyst - 0% Cs | | | |
| $C_1$–$C_3$ | 9.7 | 12.8 | 18.1 |
| $C_5$+ | 82.3 | 78.2 | 71.8 |
| Benzene | 3.58 | 4.65 | 6.06 |
| Catalyst A - 0.12% Cs | | | |
| $C_1$–$C_3$ | 8.6 | 10.3 | 11.9 |
| $C_5$+ | 84.1 | 81.6 | 78.2 |
| Benzene | 3.59 | 4.37 | 5.94 |
| Catalyst B - 0.35% Cs | | | |
| $C_1$–$C_3$ | 7.0 | 8.9 | 13.4 |
| $C_5$+ | 86.8 | 84.3 | 78.4 |

Table 2-continued

| Yields, Wt.% of Feed | Temp., °F. | | |
|---|---|---|---|
| | 925 | 950 | 975 |
| Benzene | 3.05 | 3.68 | 5.30 |
| Catalyst C - 0.41% Cs | | | |
| $C_1$-$C_3$ | 5.6 | 8.1 | 12.5 |
| $C_5$+ | 89.8 | 85.6 | 80.6 |
| Benzene | 2.69 | 3.26 | 4.01 |
| Catalyst D - 3.4% Cs | | | |
| $C_1$-$C_3$ | 2.5 | 3.5 | 5.1 |
| $C_5$+ | 95.7 | 94.5 | 92.4 |
| Benzene | 1.0 | 1.08 | 1.23 |

The foregoing results are plotted on the attached drawing and it will be seen that consistently higher benzene yields are obtained at any given $C_5$+ yield as a result of adding 0.12% to 0.41% of Cs to the base catalyst. Catalyst C, containing 0.41% Cs, gave a slightly unfavorable result at 975° F., but is advantageous at below that temperature. In all probability it would also be advantageous at above 975° F. for other feedstocks and/or operating conditions. The results for catalyst D clearly show that 3.4% Cs is highly detrimental to dehydrocyclization activity.

While it is somewhat difficult to accurately assess relative hydrocracking selectivity in the reforming of the low end point feed employed in the foregoing examples, a clear indication of desirable selectivity is found by comparing the ratios of dry gas produced vs. pentanes produced at 975° F.:

Table 3

| Catalyst | Product Mol-Ratio, $C_1$-$C_3/C_5$ |
|---|---|
| Base Catalyst, 0% Cs | 6.44 |
| A - 0.12% Cs | 4.41 |
| B - 0.35% Cs | 5.07 |
| C - 0.41% Cs | 6.13 |
| D - 3.4% Cs | 6.65 |

It will be seen that in all cases except catalyst D, the addition of Cs gave reduced dry gas make per mole of pentanes produced.

EXAMPLE 6

Another catalyst of this invention was prepared by first impregnating alumina extrudates with a solution of cesium nitrate, drying, impregnating with a solution of iridium chloride, drying again, impregnating with a solution of platinum chloride, and finally drying and calcining. The resulting catalyst contained 0.59 wt. % Pt, 0.1 wt. % Ir, 0.17 wt. % Cs and 0.8 wt. % Cl.

A feedstock consisting essentially of n-hexane was subjected to dehydrocyclization over this catalyst at 2.0 LHSV, 100 psig and 5000 SCF/B of hydrogen. The results at various temperatures were as follows:

Table 4

| Temp., °F. | Product, Wt. % of Feed | |
|---|---|---|
| | Benzene | $C_5$+ |
| 900 | 6.9 | 82.5 |
| 950 | 11.4 | 75.0 |
| 1000 | 23.9 | 58.3 |
| 1050 | 19.5 | 44.3 |

Data obtained from similar runs utilizing a Pt—Ir—$Al_2O_3$—Cl catalyst free of Cs, but (by an inadvertence in its preparation) containing only about 0.3 wt. % Pt, clearly indicate that much improved selectivity was achieved by the addition of Cs, but the relative activities are probably not comparable due to the differences in Pt content.

Results substantially similar to those presented in the foregoing examples are obtained when equivalent atomic proportions of Rh are substituted for the Ir component of the catalysts. The principal function of the Ir and/or Rh component is to increase stability of the catalysts.

The following claims and their obvious equivalents are believed to define the true scope of the invention.

We claim:

1. A dehydrocyclization-reforming catalyst composition comprising alumina and supported thereon about 0.1-2 wt. % Pt, about 0.1-3 wt. % Cl and sufficient Cs to provide a Cs/Cl atomic ratio between about 0.005 and 0.2.

2. A catalyst as defined in claim 1 wherein the Cs/Cl atomic ratio therein is between about 0.01 and 0.15.

3. A catalyst as defined in claim 1 containing about 0.5-2.0 wt. % Cl.

4. A catalyst as defined in claim 3 wherein the Cs/Cl atomic ratio is between about 0.01 and 0.15.

5. A dehydrocyclization-reforming catalyst composition comprising alumina and supported thereon about 0.1-2 wt. % Pt, about 0.1-3 wt. % Cl, about 0.02-0.5 wt. % of Ir and/or Rh and sufficient Cs to provide a Cs/Cl atomic ratio between about 0.005 and 0.2.

6. A catalyst as defined in claim 5 wherein the Cs/Cl atomic ratio therein is between about 0.01 and 0.15.

7. A catalyst as defined in claim 5 containing about 0.5-2.0 wt. % Cl.

8. A catalyst as defined in claim 7 wherein the Cs/Cl atomic ratio is between about 0.01 and 0.15.

9. A catalyst as defined in claim 5 comprising Ir.

10. A catalyst as defined in claim 9 wherein the Cs/Cl atomic ratio is between about 0.01 and 0.15.

* * * * *